US010138467B2

(12) United States Patent
Broly et al.

(10) Patent No.: US 10,138,467 B2
(45) Date of Patent: Nov. 27, 2018

(54) MEDIUM FOR HIGH PERFORMANCE MAMMALIAN FED-BATCH CULTURES

(71) Applicant: ARES TRADING S.A., Aubonne (CH)

(72) Inventors: Herve Broly, Châtel-St-Denis (CH); Matthieu Stettler, Vucherens (CH); Martin Jordan, Ecublens (CH); Arnaud Perilleux, Granges (Veveyse) (CH); Yolande Rouiller, Lausanne (CH)

(73) Assignee: ARES TRADING S.A., Aubonne (CH)

( * ) Notice: Subject to any disclaimer, the term of this patent is extended or adjusted under 35 U.S.C. 154(b) by 2 days.

(21) Appl. No.: 15/028,989

(22) PCT Filed: Apr. 3, 2014

(86) PCT No.: PCT/EP2014/056650
§ 371 (c)(1),
(2) Date: Apr. 13, 2016

(87) PCT Pub. No.: WO2015/055324
PCT Pub. Date: Apr. 23, 2015

(65) Prior Publication Data
US 2016/0264940 A1    Sep. 15, 2016

Related U.S. Application Data

(60) Provisional application No. 61/890,807, filed on Oct. 14, 2013.

(51) Int. Cl.
*C12N 5/00* (2006.01)
*C12N 5/16* (2006.01)
*C12N 5/071* (2010.01)

(52) U.S. Cl.
CPC .......... *C12N 5/0682* (2013.01); *C12N 5/005* (2013.01); *C12N 5/0031* (2013.01); *C12N 5/0037* (2013.01); *C12N 5/16* (2013.01); *C12N 2500/12* (2013.01); *C12N 2500/14* (2013.01); *C12N 2500/16* (2013.01); *C12N 2500/22* (2013.01); *C12N 2500/24* (2013.01); *C12N 2500/32* (2013.01); *C12N 2500/35* (2013.01); *C12N 2500/38* (2013.01); *C12N 2500/40* (2013.01); *C12N 2500/46* (2013.01); *C12N 2500/60* (2013.01); *C12N 2500/90* (2013.01); *C12N 2500/95* (2013.01); *C12N 2500/99* (2013.01); *C12N 2510/02* (2013.01)

(58) Field of Classification Search
None
See application file for complete search history.

(56) References Cited

U.S. PATENT DOCUMENTS

| 4,767,704 | A | 8/1988 | Cleveland et al. |
| 8,093,052 | B2 * | 1/2012 | Fonta .................... C07K 14/59 435/404 |
| 2006/0094113 | A1 | 5/2006 | Epstein et al. |
| 2008/0227136 | A1 * | 9/2008 | Pla .......................... C07K 16/00 435/29 |
| 2013/0071906 | A1 * | 3/2013 | Grillberger .......... C12N 9/6489 435/226 |

FOREIGN PATENT DOCUMENTS

EP    2 221 361    8/2010

OTHER PUBLICATIONS

Richardson, Iron and gallium increase iron uptake from transferrin by human melanoma cells : further examination of the ferric ammonium citrate-activated iron uptake process, Biochimica et Biophysica Acta 1536 (2001) 43-54.*
Didier, C. et al. "Crossed mixture design and multiple response analysis for developing complex culture media used in recombinant protein production" *Chemometrics and Intelligent Laboratory Systems*, Mar. 1, 2007, pp. 1-9, vol. 86, No. 1.
Jordan, M. et al. "Cell culture medium improvement by rigorous shuffling of components using media blending" *Cytotechnology*, 2013, pp. 31-40, vol. 65, No. 1.
Kim, D. Y. et al. "Development of serum-free media for a recombinant CHO cell line producing recombinant antibody" *Enzyme and Microbial Technology*, Jul. 3, 2006, pp. 426-433, vol. 39, No. 3.
Rispoli, F. et al. "A New Efficient Mixture Screening Design for Optimization of Media" American Institute of Chemical Engineers, 2009, pp. 980-985, vol. 25, No. 4.
Rodrigues, M. E. et al. "Comparison of commercial serum-free media for CHO-K1 cell growth and monoclonal antibody production" *International Journal of Pharmaceutics*, Nov. 1, 2012, pp. 303-305, vol. 437, No. 1-2.
Rouiller, Y. et al. "A high-throughput media design approach for high performance mammalian fed-batch cultures" *mAbs*, Jun. 2013, pp. 501-511, vol. 5, No. 3.
Xing, Z. et al. "Optimizing amino acid composition of CHO cell culture media for a fusion protein production" *Process Biochemistry*, Mar. 21, 2011, pp. 1423-1429, vol. 46, No. 7.
Written Opinion in International Application No. PCT/EP2014/056650, dated Aug. 21, 2014, pp. 1-6.

* cited by examiner

*Primary Examiner* — Nancy J Leith
(74) *Attorney, Agent, or Firm* — Saliwanchik, Lloyd & Eisenschenk

(57) ABSTRACT

The present invention relates to new serum- and protein-free culture media. These media are high performance culture media, which notably improve mammalian fed-batch cultures. The present invention also relates to methods for preparing and/or designing the medium, and methods of use thereof.

9 Claims, 7 Drawing Sheets

MEDIUM FOR HIGH PERFORMANCE MAMMALIAN FED-BATCH CULTURES

CROSS-REFERENCE TO RELATED APPLICATION

This application is the U.S. national stage application of International Patent Application No. PCT/EP2014/056650, filed Apr. 3, 2014.

FIELD OF INVENTION

The present invention relates to new serum- and protein-free culture media. These media are high performance culture media, which notably improve mammalian fed-batch cultures. The present invention also relates to methods for preparing and/or designing the culture medium, and methods of use thereof. These culture media and methods can be applied to the culture of any mammalian cells, such as Chinese hamster ovary (CHO) cells, and can be used in bioreactors of all kinds.

BACKGROUND OF THE INVENTION

The biotechnology industry is strongly motivated to develop high performance processes in a minimal time frame to meet increasing market demands and reduce manufacturing costs. Many efforts have focused on media optimization, since a well-balanced media composition is essential for two major elements of a fed-batch process: maximal viable cell density and productivity. See Jerums and Yang (2005) BioProcess International, 3:38-44; Zhang et al. (2008) BioPharm International, 21:60-8; Hodge (2005) BioPharm. International., 18:1-4; and Li, F. et al. (2010) mAbs, 2:455-477.

Process development for protein therapeutics is increasingly dependent on high-throughput (HT) technologies to accelerate the screening of many conditions and the optimization of cell culture process outputs. Automated HT experimentation provides opportunities to explore a large design space by using full factorial experimental design and to decrease costs by reducing raw materials, culture media, labor and time. See Amanullah, A. et al. (2010) Biotechnol. Bioeng., 106:57-67; Bareither, R. and Pollard, D. (2011) Biotechnol. Prog, 27:2-14; and Barrett, T. A. et al. (2010) Biotechnol. Bioeng., 105:260-75. Among the numerous HT systems available, microwell plates, which were first used for analytical applications, have become an important tool for microbial and mammalian cell culture applications during the last ten years. Intense efforts were made to understand suspension culture conditions within these devices, by characterizing oxygen mass transfer rates and mixing conditions in particular, to confirm their efficiency in supporting cell culture needs. Their integration into standard lab automation liquid handling platforms that enable simultaneous loading, sampling and feeding of cells, and the incorporation of fluorescence patch sensors into wells to perform pH, dissolved oxygen (DO), and optical density (OD) measurements, have made them an efficient scale-down tool for bioprocess development studies. See Baboo et al. (2012) Biotechnol. Prog., 28:392-405; Chen, A. et al. (2009) Biotechnol. Bioeng., 102:148-60; Duetz, W. A. (2007) Trends Microbiol., 15:469-75; Funke, M. et al. (2009) Biotechnol. Bioeng, 103:1118-28; Micheletti, M. and Lye, G. J. (2006) Curr. Opin. Biotechnol., 17:611-618; and Wen Y et al. (2012) Process Biochem., 47:612-618.

Medium optimization is an important step in process development as medium components at suboptimal concentrations might be limiting for cell growth or productivity, and therefore might directly affect process performance. See Kim, D. Y. et al. (2005) Cytotechnol., 47:37-49. On the other hand, medium components might also have an effect on secreted proteins, more particularly on their glycosylation, which is essential for their bioactivity and stability in vivo. See Gawlitzek, M. et al. (2009) Biotechnol. Bioeng., 103: 1164-1175; and Hossler, P. et al. (2009) Glycobiology, 19:936-49. The traditional strategy used for culture medium development relies on the variation of one factor at a time (OFAT) while keeping the others constant. This is laborious, time-consuming, and does not account for synergistic interactions of components. Therefore, new technologies and methods involving design of experiments (DoE) and statistical analysis have been implemented.

These DoE and statistical analysis technologies enable the testing of several components at a time and identification of their interactions. See Lee, G. M. et al. (1999) J. Biotechnol., 69:85-93; Sandadi, S. et al. (2006) Biotechnol. Prog., 22:595-600; and Zhang, H. et al. (2012) Cytotechnol. published online 21 Aug. 2012. Several strategies for medium optimization have been described. See Jerums, M. and Yang, X. (2005); Zhang, M. et al. (2008). For example, optimization can be based on spent medium analysis, see Xie, L. and Wang, D. I. (1994) Biotechnol Bioeng, 43:1164-74. Optimization can also be based on metabolite flux analyses or on metabolomics, which allow rebalance of components in subsequent experiments, see Dietmair, S. et al. (2012) Biotechnol. Bioeng., 109:1404-14; Selvarasu, S. et al. (2012) Biotechnol. Bioeng., 109:1415-1429; and Xing, Z. et al. (2011) Process Biochem., 46:1423-1429. On the other hand, in the high-throughput approach where statistical DoE is linked to automation and small cell culture devices, enable testing of several hundreds of media formulations, tests are usually performed by monitoring critical process outputs (e.g., cell growth, protein titers). This enables testing of several hundreds of media formulations, See Barrett et al. (2010); Didier, C. et al. (2007) Chemom. Intell. Lab. Syst., 86:1-9; Girard, P. et al. (2001) Biochem. Eng. J., 7:117-119; and Hodge, G. (2005) Biopharm International, 18:1-4.

When working with complex biological systems such as recombinant mammalian cell cultures, mixture designs to evaluate combinations of different defined formulations can be an important tool for media optimization. See Jerums and Yang (2005); Didier et al. (2007); and Rispoli, F. and Shah, V. (2009) Biotechnol. Prog., 25:980-985. This approach is particularly interesting when testing numerous components because it avoids component solubility issues that might occur using factorial designs. Optimal concentration ranges of the various culture medium components can be identified by evaluating the performance of the various new mixtures obtained by media blending. Jordan et al. recently described a novel high-throughput method based on an extended media blending strategy that was used to reshuffle 20 amino acids in one round of experiments. See Jordan, M. et al. (2013) Cytotechnol., 65:31-40. Several significantly improved viable cell densities and titers of a Chinese hamster ovary (CHO) cell batch culture producing a monoclonal antibody (mAb) resulted from 192 mixtures prepared by media blending from 10 formulations.

Usually, medium and feed development of a fed-batch process are performed sequentially because of the large number of experiments required for a simultaneous optimization. For example, Zhang et al. (2012) sequentially developed a medium and a feed for a fed-batch process for CHO cells expressing a recombinant antibody. Zhang et al. used a Plackett-Burman design to screen active factors for cell growth and antibody production, followed by a central composite design to optimize their concentration, and by a feeding design based on stoichiometric ratios of different nutrients improving productivity. Nevertheless, the outcome of a successive optimization strategy might not always be ideal because basal medium and feed medium might have interrelated impacts on cell culture performance. Indeed, an improved basal medium can alter the metabolism and growth of cells, which then may require a modified feed. Therefore, sequential optimization of some elements has to be repeated, or sequential medium and feed optimization have to be followed by a final round of integrated optimization of feed and process settings, as proposed by Jiang Z et al. (2012) BioProcess International, 10:40-45.

Other groups have focused on the development of supplement blends. For instance, WO 12/078270 discloses screening methods to determine cell culture media supplements or supplement blends with enhanced performance characteristics. It describes, in particular, a supplement or combination of supplements comprising one, two or more components, to be added to culture media, case by case.

Numerous documents have described mammalian cell culture media. For instance, the application EP 2154244 discloses media for culturing cells, the media having at least 1 mM serine, at least 1 mM tyrosine and at least 0.4 mM cysteine. This application is silent with regard to the specific concentrations of the other components needed to obtain an optimized culture medium. The patent, EP481791, is related to culture media free from protein, lipid and carbohydrate isolated from an animal source, but instead uses recombinant protein sources, for instance, recombinant insulin. In addition, this patent discloses specific ranges of concentrations for the amino acids to be included in the culture media. Another example is U.S. Pat. No. 6,048,728, which describes a culture medium comprising at least one of glutamine, glutamate and asparagine at a concentration of at least 8 mM, tryptophan, another amino acid, and phospholipid precursors comprising at least choline and ethanolamine. Still another example is WO 98/45411, which discloses culture media with specific amino acid concentrations.

However, there is still a need to develop high performing processes in a minimal time frame to meet increasing market demands and reduce manufacturing costs. Developing high performing processes implicitly means developing high performing culture media, having no risk of contamination (i.e., being serum- and protein-free).

SUMMARY OF THE INVENTION

One aspect of the present invention is new serum- and protein-free culture media. These culture media are considered high performance since they are able to improve the performance of classic mammalian media, such as a classic Chinese hamster ovary (CHO) medium. For example, the media of the present invention can be produced at higher yield and in less time.

Also described are new blending designs for the development of media, including the development of media for a fed-batch cell culture. These designs enable the optimization of all medium components of a proprietary or a classic medium in one single experiment.

The present invention further includes methods for preparing the medium, and methods of use thereof. The culture media and the methods according to the invention can be applied to the culture of any mammalian cells, in bioreactors of all kinds. Preferably they are applied to CHO cells in fed-batch bioreactors.

One embodiment of the present invention is thus a medium for mammalian cell culture, which is serum- and protein-free, and comprises: $NaH_2PO_4$, L-Leucine, L-Lysine, L-Methionine, L-Glutamic acid, L-Phenylalanine, L-Proline, L-Threonine, L-Tryptophan, L-Valine, magnesium sulfate, calcium chloride, myo-inositol, sodium pyruvate, D-Biotin, choline chloride, L-Asparagine, folic acid, niacinamide (B3), D-pantothenic acid×½ Ca, L-Serine, potassium chloride, pyridoxine, L-Aspartic acid, riboflavin, thiamine, ferric ammonium citrate, vitamin B12, hypoxanthine, thymidine, putrescine, ethanolamine, zinc sulfate, cupric sulfate, poloxamer (PLURONIC), L-tyrosine, sodium selenite, L-Alanine, L-arginine, L-Cysteine, L-Histidine and L-Isoleucine. The medium may further comprises glucose, $NaHCO_3$, or a combination thereof, as well as NaCl and NaOH. When added, NaCl and/or NaOH are used for osmolality and pH adjustments.

In one embodiment, the concentrations of the media components range as follows:
$NaH_2PO_4$: from 1.7 to 10;
L-Leucine: from 2 to 9 mM;
L-Lysine: from 1 to 6 mM;
Glycine: from 0 to 3 mM;
L-Methionine: from 0.4 to 2 mM;
L-Glutamic acid: from 1 to 4 mM;
L-Phenylalanine: from 0.5 to 3 mM;
L-Proline: from 0.7 to 6 mM;
L-Threonine: from 0.7 to 6 mM;
L-Tryptophan: from 0.5 to 2 mM;
L-Valine: from 1 to 7 mM;
Magnesium Sulfate: from 0.1 to 1.5 mM;
Calcium Chloride: from 0.1 to 1.05 mM;
Myo-Inositol: from 0.07 to 0.7 mM;
Sodium pyruvate: from 0.8 to 4 mM;
D-Biotin: from 0.0008 to 0.01 mM;
Choline Chloride: from 0.1 to 1 mM;
L-Asparagine: from 3 to 9 mM;
Folic acid: from 0.006 to 0.04 mM;
Niacinamide (B3): from 0.03 to 0.15 mM;
D-pantothenic acid×½ Ca: from 0.015 to 0.15 mM;
L-Serine: from 1 to 8 mM;
Potassium Chloride: from 1 to 10 mM;
Pyridoxine: from 0.005 to 0.05 mM;
L-Aspartic acid: from 0.8 to 2.4 mM;
Riboflavin: from 0.0003 to 0.003 mM;
Thiamine: from 0.008 to 0.04 mM;
Ferric ammonium citrate: from 1 to 10 mg/L;
Vitamin B12: from 0.0003 to 0.004 mM;
Hypoxanthine: from 0.008 to 0.04 mM;
Thymidine: from 0.0015 to 0.006 mM;
Putrescine: from 0.006 to 0.03 mM;
Ethanolamine: from 0.1 to 0.5 mM;
Zinc Sulfate: from 0.004 to 0.02 mM;
Cupric sulfate: from to 0.00004 to 0.0008 mM;
poloxamer (PLURONIC): from 0.5 to 2.0 g/L;
L-Tyrosine: from 0.7 to 3 mM;
Sodium Selenite: from 0.00001 to 0.00006 mM;
L-Alanine: from 0 to 3 mM;
L-Arginine: from 1 to 3 mM;
L-Cysteine: from 1 to 3 mM;
L-Histidine: from 0.4 to 3 mM; and
L-Isoleucine: from 1 to 6 mM.

When the medium further comprises glucose $NaHCO_3$, or a combination thereof, these components are preferably kept constant. In one embodiment, the glucose is kept at a concentration of approximately 6 g/L (i.e., 33 mM) and the NaHCO$_3$ is kept at a concentration of approximately 2 g/L (i.e., 23.8 mM).

Another embodiment of the invention the osmolarity of the medium according to the present invention is from 300 to 330 mOsm/kg, preferably at about or at 305 to 320 mOsm/kg, even preferably at about or at 315 mOsm/kg.

The pH of the medium according to the present invention ranges from about 6 to about 8, preferably from about 6.5 to about 7.5, and even more preferably at about or at 6.8, 6.9, 7.0, 7.1 or 7.2.

DETAILED DESCRIPTION OF THE PREFERRED EMBODIMENTS OF THE INVENTION

Figure 1:
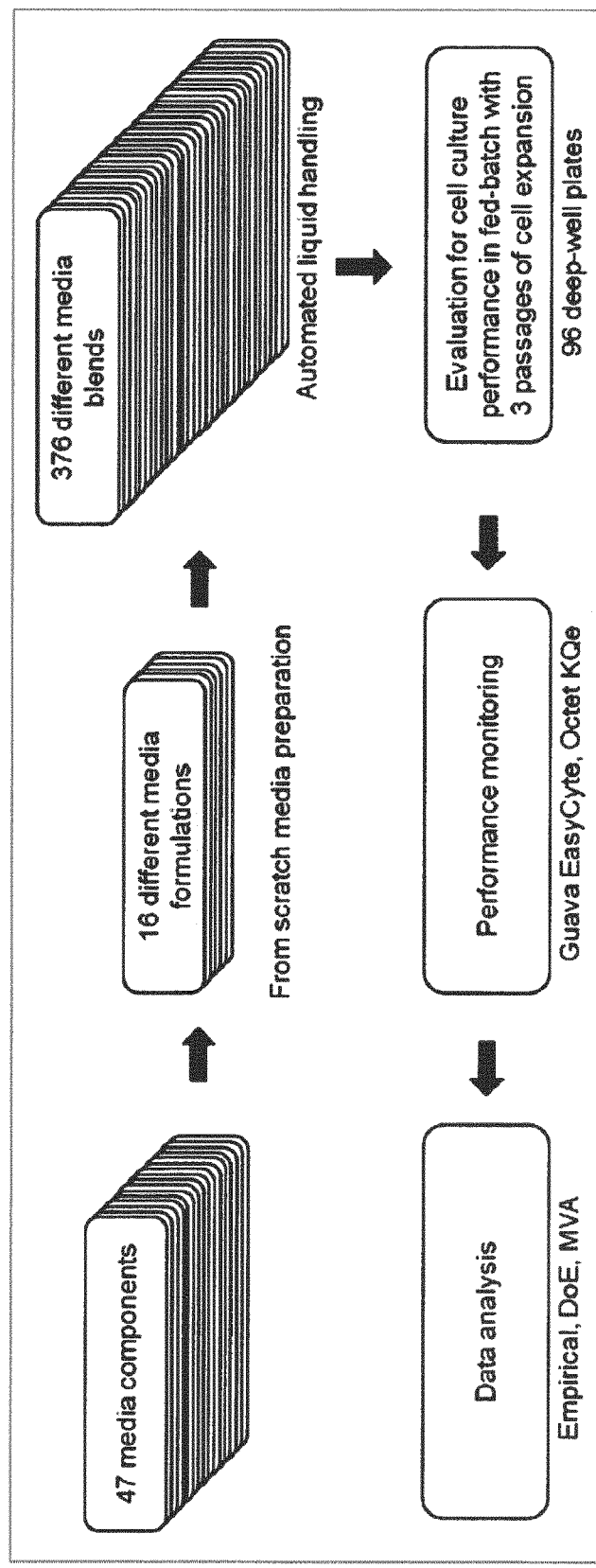
FIG. 1 shows a high-throughput media blending method in accordance with an embodiment of the present invention.

The terms "cell culture medium," "culture medium," "medium," and "media" refer to any medium in which cells of any type can be cultured.

The term "bioreactor" refers to any system in which cells can be cultured. This term includes but is not limited to flasks, stationary flasks, spinner flasks, shake tubes, shake bottles, wave bags, fiber bioreactors, fed batch bioreactors or high capacity bioreactors.

A "classic medium" or "basal medium" refers to a cell culture medium that contains all of the essential ingredients useful for cell metabolism. This includes for instance amino acids, lipids, carbon source, vitamins and mineral salts. DMEM (Dulbeccos' Modified Eagles Medium), RPMI (Roswell Park Memorial Institute) medium and medium F12 (Ham's F12 medium) are examples of classic media.

A "chemically defined medium," "chemically defined basal medium," and "CDM" refer to a medium in which all of the components can be described in terms of their chemical formulas and are present in known concentrations.

The term "fed-batch culture" refers to a continuous method of growing cells, where there is a bolus or continuous media supplementation to replenish the media that is consumed. This cell culture technique has the potential to achieve high cell densities on the order of greater than 10×10$^6$ to 30×10$^6$ cells/ml, depending on the media formulation, cell line, and other cell growth conditions. A biphasic culture condition can be created and sustained by a variety of feed strategies and media formulations.

One aspect of the present invention is new serum- and protein-free culture media. These media outperform classic mammalian media, such as classic Chinese Hamster Ovary (CHO) medium, in several respects. For example, when a culture medium of the present invention is used in a fed-batch process, the process produces proteins at high yield and in less time.

The media according to the present invention are chemically well-defined, and free of serum and protein. These properties allow the media according to the present invention to produce proteins, such as recombinant proteins, at higher yield. These media have uniform properties with less variation among lots. Using the media ensures that a protein, such as a recombinant protein, having uniform properties can be obtained. The media are thus suitable for industrial manufacture of proteins, such as recombinant proteins (e.g., a cytokine, a growth factor, a hormone, an antibody or a fragment thereof). Since the media according to the present invention are serum- and protein-free, there is no risk of viral contamination.

An exemplary embodiment of the invention further provides methods of preparing a medium, by mixing the various elements together in a liquid. The liquid may be, but is not limited to, water or a classic medium (basal medium). If a basal medium is used, the quantity of each component to be added will depend on the initial concentration in the basal medium, in order to fit to the final concentrations recited in Table 2.

TABLE 2

Tested component concentration ranges: 43 out of 47 medium components were tested at three levels, level 0 (low), level 1 (intermediate) and level 2 (high). Level 1 is not shown but represents an intermediate concentration between level 0 and level 2 for each component. Glucose (6 g/L) and NaHCo3 (2 g/L) were kept constant, while NaCl and NaOH were used for osmolality and pH adjustments, respectively.

| Components | Level 0 (mM) | Level 2 (mM) |
|---|---|---|
| NaH$_2$PO$_4$ | 1.7 | 10 |
| L-Leucine | 2 | 9 |
| L-Lysine | 1 | 6 |
| Glycine | 0 | 3 |
| L-Methionine | 0.4 | 2 |
| L-Glutamic acid | 1 | 4 |
| L-Phenylalanine | 0.5 | 3 |
| L-Proline | 0.7 | 6 |
| L-Threonine | 0.7 | 6 |
| L-Tryptophan | 0.5 | 2 |
| L-Valine | 1 | 7 |
| Magnesium Sulfate | 0.1 | 1.5 |
| Calcium Chloride | 0.1 | 1.05 |
| Myo-Inositol | 0.07 | 0.7 |
| Sodium pyruvate | 0.8 | 4 |
| D-Biotin | 0.0008 | 0.01 |
| Choline Chloride | 0.1 | 1 |
| L-Aspargine | 3 | 9 |
| Folic acid | 0.006 | 0.04 |
| Niacinamide (B3) | 0.03 | 0.15 |
| D-pantothenic acid × ½ Ca | 0.015 | 0.15 |
| L-Serine | 1 | 8 |
| Potassium Chloride | 1 | 10 |
| Pyridoxine | 0.005 | 0.05 |
| L-Aspartic acid | 0.8 | 2.4 |
| Riboflavin | 0.0003 | 0.003 |
| Thiamine | 0.008 | 0.04 |
| Ferric ammonium citrate | 1 mg/L | 10 mg/L |

TABLE 2-continued

Tested component concentration ranges: 43 out of 47 medium components were tested at three levels, level 0 (low), level 1 (intermediate) and level 2 (high). Level 1 is not shown but represents an intermediate concentration between level 0 and level 2 for each component. Glucose (6 g/L) and NaHCo3 (2 g/L) were kept constant, while NaCl and NaOH were used for osmolality and pH adjustments, respectively.

| Components | Level 0 (mM) | Level 2 (mM) |
|---|---|---|
| Vitamin B12 | 0.0003 | 0.004 |
| Hypoxanthine | 0.008 | 0.04 |
| Thymidine | 0.0015 | 0.006 |
| Putrescine | 0.006 | 0.03 |
| Ethanolamine | 0.1 | 0.5 |
| Zinc Sulfate | 0.004 | 0.02 |
| Cupric sulfate | 0.00004 | 0.0008 |
| Pluronic | 0.5 g/L | 2.0 g/L |
| L-Tyrosine | 0.7 | 3 |
| Sodium Selenite | 0.00001 | 0.00006 |
| L-Alanine | 0 | 3 |
| L-Arginine | 1 | 3 |
| L-Cysteine | 1 | 3 |
| L-Histidine | 0.4 | 3 |
| L-Isoleucine | 1 | 6 |

The present invention further describes a new blending design for the development of an improved culture medium, notably for fed-batch cell culture processes, enabling the optimization of all medium components of a classic or a proprietary medium in one single experiment. The ability to simultaneously test all media components presents the advantage that no potentially critical factors are missed.

Also described herein is a high-throughput media blending method for developing and/or optimizing a (basal or classic) culture medium, comprising:
a) selecting the media components or selecting a basal medium for optimization, wherein the medium for optimization is well characterized;
b) selecting 3 levels of concentration for each of the components;
c) preparing a set of media formulations with the selected components at different concentrations;
d) mixing the different formulations, at different concentrations, to obtain different media blends;
e) evaluating each blend for cell culture performance, wherein the cell culture is a mammalian cell culture;
f) monitoring the performance of each blend on cell culture;
g) analyzing the data obtained in step f); and
h) determining one or more final culture medium (media).

In an exemplary embodiment, the final culture medium obtain in the step (h) is optimized compared to other media or compared to the medium from which it has been optimized. The final culture medium is for instance to be used as a cell expansion and/or fed-batch culture medium. The media blends of step (c) can further comprise glucose NaHCO₃, NaCl and/or NaOH, or a combination thereof among other components that can be added depending on the cells to be cultured, or depending on the cell culture conditions.

In order to evaluate each blend for cell culture performance (step e), each different media blend has to be inoculated with mammalian cells, and said mammalian cells have to be cultured in said media blend.

In another exemplary embodiment, the present invention relates to a high-throughput media blending method for developing and/or optimizing a culture medium, comprising:

a) selecting the media components or selecting a medium for optimization, wherein the medium for optimization is well characterized components;
b) selecting 3 levels of concentration for each of the components;
c) preparing a set of media formulations with the selected components at different concentrations;
d) mixing the different formulations, at different concentrations, to obtain different media blends;
e) evaluating each blend for cell culture performance, wherein the cell culture is a mammalian cell culture;
f) monitoring the performance of each blend on cell culture;
g) analyzing the data obtained in step f);
h) determining the key components for further optimization;
i) repeating steps b) to g) based on the information obtained in step h);
j) optionally repeating steps h) and i); and
k) determining one or more final culture medium.

In one exemplary embodiment, the final culture medium obtained in step (k) is optimized compared to other media or compared to the medium from which it has been optimized. The final culture medium is for instance to be used as a cell expansion and/or fed-batch culture medium. In addition, the media blends of step (c) can further comprise glucose, NaHCO₃, NaCl and/or NaOH or a combination thereof, among other components that can be added depending on the cells to be cultured, or depending on the cell culture conditions.

In order to evaluate each blend for cell culture performance (step e), each different media blend has to be inoculated with mammalian cells, and said mammalian cells have to be cultured in said media blend.

In an exemplary embodiment, the key component(s) of step h) comprise at least one of the components of ferric ammonium citrate, pantothenic acid, valine, methionine, arginine, biotin, serine, aspartic acid, asparagine, cupric sulfate, cysteine, Vitamin B12, sodium selenite, or combinations thereof. Indeed, ferric ammonium citrate, pantothenic acid, valine, methionine, arginine, biotin and serine have been shown to have an influence on the model for the titer, whereas aspartic acid, asparagine, cupric sulfate, cysteine, Vitamin B12 and sodium selenite have been shown to correlate with an important factor in the MVA (see Examples, Data Analysis Process).

The design methods according to the invention can be applied to the design and/or optimization of culture media for any mammalian cells, in bioreactors of all kinds. Preferably the mammalian cell has been modified in order to express and produce a protein (a recombinant protein), such as a cytokine, a growth factor, a hormone, an antibody or a fragment thereof. In one embodiment, the mammalian cell is a CHO cell or a recombinant CHO cell.

The evaluation of the cell culture performance can be done by measuring viable cell density (VCD), titer, integral viable cell density (IVC), population doubling level (PDL) and/or viability. These measurements can be done using any standard method that is well known to the skilled person.

The culture media described herein can be used for culturing any mammalian cells. They are particularly suitable for culturing CHO cells or recombinant CHO cells, notably in fed-batch bioreactors. In one embodiment, the mammalian cell, such as a CHO cell, is a recombinant cell which has been modified in order to express and produce a protein (a recombinant protein), such as a cytokine, a growth factor, a hormone, an antibody or a fragment thereof.

In a further exemplary embodiment, the present invention describes a process for producing a given protein in a mammalian cell, the process comprising growing the cells in the medium according to the present invention and recovering the given protein produced by the mammalian cell. Also recited is a process for producing a given protein, comprising the steps of: a) culturing a mammalian cell that is capable of producing the given protein, such as a recombinant protein, wherein the culture is performed in one of the media according to the present invention, and b) recovering the given protein produced by the mammalian cell. In one embodiment, the mammalian cell has been modified in order to express and produce a protein (a recombinant protein), such as a cytokine, a growth factor, a hormone, an antibody or a fragment thereof. In another embodiment, the mammalian cell is a CHO cell or a recombinant CHO cell.

In another exemplary embodiment, a method for culturing mammalian cells to obtain a product is described. The method comprises growing the cells in one of the media according to the present invention. Further described herein is a method of culturing a mammalian cell, the method comprising the steps of a) culturing a mammalian cell that is capable of producing a given protein, such as a recombinant protein, wherein the culture is performed in one of the media according to the present invention, for a period sufficient to enable the mammalian cell to grow sufficiently or during a period sufficient to enable adequate production of the given protein and b) recovering the given protein produced by the mammalian cell. In one embodiment, the mammalian cell has been modified in order to express and produce a protein (a recombinant protein), such as a cytokine, a growth factor, a hormone, an antibody or a fragment thereof. Preferably the mammalian cell is a CHO cell or a recombinant CHO cell.

Starting from a proprietary medium composed of 47 components, 16 formulations were designed by varying 43 of the components over 3 different levels. The only factors excluded from the blending design were glucose, which was part of the feed and was not limiting during the first 3 days of culture, NaOH, which was needed for pH adjustment, $NaHCO_3$ as the principal pH buffer, and NaCl for osmolality adjustment. Media blending, based on a custom-made mixture DoE considering binary blends, resulted in 376 blends that were tested in 96-DWP on process performance of a CHO fed-batch culture. Testing the different blends during the expansion phase ensures that the best identified production media can also be used as expansion media. Indeed, some blends were already able to increase cell growth by 20% during the cell expansion phase, and this increase was confirmed during the production phase. Regarding the titer, an important improvement of up to 40% was observed with certain blends. Globally, best conditions generally improved IVC, titer and specific productivity, but some conditions showed no IVC increase but an increase in titer and specific productivity.

The strategy used for data analyses included 3 levels. The first level was an empirical analysis of the effect of each media blend on the cell culture process performance. By scoring and ranking all blending conditions regarding their potential to improve process outputs, best conditions became readily available and could be further tested at larger scale for confirmation. This method represents a simple and quick way for medium optimization without the use of complex statistical methodologies. The two other levels of analyses used statistical tools, enabling a more in-depth evaluation. By using mathematical models, the first tool, Design Expert software, enabled prediction of best mixtures maximizing final PDL, IVC and titer. A great advantage of this method is that several criteria could be analyzed together to determine synergistic responses between criteria. Moreover, it allowed ranking of the initial 16 formulations, e.g., to identify the formulations that were systematically present in poor performing mixes and could be replaced by others to be tested in a new DoE. The modelling tool is also useful to simulate untested new mixtures with different blending ratios and not limited to two formulations, which will enable the prediction of the best possible blend.

The ultimate level of analysis based on MVA used SIMCA-P++ software. The model created for the titer using partial least square regression enabled identification of ferric ammonium citrate, pantothenic acid, valine, methionine, arginine, biotin and serine as factors with the most influence on the titer, while other factors such as aspartic acid, asparagine, cupric sulfate, cysteine, Vitamin B12 and sodium selenite were selected because they correlated with an important factor in the MVA. It should be noted that we actually cannot distinguish between a true effect or a "false" effect due to such a correlation. The benefit of this third method is that it enables the identification of key media components that can be further evaluated, and should lead to the identification of new media formulations with potentially improved performance.

In conclusion, the high-throughput media blending approach described herein is a robust and rapid method for medium optimization of a fed-batch process. Data analysis by simple ranking based on critical process outputs, e.g., cell growth, viability, titer, provides an easy and quick tool to determine best performing media formulations among almost 400 different blends, which can be rapidly confirmed at larger scales. On the other hand, statistical tools enable a more in-depth analysis, allowing prediction of best performing media formulations and identification of critical media components for further optimization. Compared with traditional medium development strategies, this method greatly reduces costs and development time and enhances the possibility of achieving an improved and more consistent performance within one experiment. The whole media blending process, including data analysis, was performed within 6 weeks. This method can also be applied to feed development and opens new perspectives for fed-batch process development and optimization, and for other activities such as cell line screening and cell line stability studies.

EXAMPLES

Materials and Methods

Media Formulation Preparation.

Sixteen formulations were prepared by weighing individual components. For each formulation, the glucose concentration was fixed at 33.3 mM to prevent any limitation during the first 3 days of culture; the NaOH concentration was adjusted to obtain a pH of 7.0 before $NaHCO_3$ addition; the $NaHCO_3$ concentration was fixed at 23.8 mM to maintain buffering capacity; and the NaCl concentration was adjusted to reach an osmolality of approximately 315 mOsm/kg.

Automated Media Blending.

High-throughput media blending was performed on a liquid handling workstation (Biomek FX, Beckman-Coulter, Inc. Fullerton, Calif. USA). A total of 376 mixtures were directly blended into five square-shaped 96-DWP (Greiner Bio-One #780271). On each plate, 16 wells were kept available for reagents necessary for titer determination. The 16 formulations were blended following a custom-made mixture DoE with binary blends. The candidate points of the design were vertices (1 formulation at 100%), center of edges (2 formulations at 50%), and third of edges (2 formulations, one at 33% and the other at 67%). In addition to the 376 mixtures, 20 controls were performed to assess experimental and plate-to-plate variability. Controls were either proprietary medium (Ctrl 1: this reference medium is not part of the media blending design and its exact composition is undisclosed) or F2 formulation (Ctrl 2: intermediate level for each component).

performed with the robotic platform. The plates were then incubated with vented lids to minimize evaporation (Duetz (2007) Trends Microbiol., 15:469-475) in a shaker incubator at 37° C., 5% $CO_2$, 90% humidity and 320 rpm agitation (ISF1-X, Kuhner AG). Three passages were performed under the same conditions for each of the different media mixtures, on days −5, −3 and 0 (day of the start of the fed-batch). At each passage, the cells were diluted to 0.75× $10^6$ cells/mL and re-incubated in a new set of five 96-DWP containing media blends and controls.

TABLE 1

Media formulation design: This matrix shows 16 media formulations (F1-F16) designed with 43 components (C1-C43). Values 0 (low), 1(mid) and 2 (high) represent relative concentrations of each component. except for F1, F2 and F3 with all components at the same level, each formulation was randomly designed regarding each component level

| | F1 | F2 | F3 | F4 | F5 | F6 | F7 | F8 | F9 | F10 | F11 | F12 | F13 | F14 | F15 | F16 |
|---|---|---|---|---|---|---|---|---|---|---|---|---|---|---|---|---|
| C1 | 0 | 1 | 2 | 0 | 0 | 0 | 0 | 1 | 1 | 1 | 1 | 1 | 2 | 2 | 2 | 2 |
| C2 | 0 | 1 | 2 | 2 | 1 | 0 | 0 | 0 | 0 | 1 | 1 | 2 | 2 | 0 | 1 | 2 |
| C3 | 0 | 1 | 2 | 2 | 2 | 0 | 1 | 0 | 2 | 2 | 1 | 0 | 2 | 2 | 0 | 0 |
| C4 | 0 | 1 | 2 | 2 | 1 | 1 | 2 | 2 | 1 | 0 | 2 | 0 | 0 | 0 | 1 | 2 |
| C5 | 0 | 1 | 2 | 2 | 2 | 0 | 1 | 2 | 0 | 2 | 0 | 0 | 1 | 1 | 1 |
| C6 | 0 | 1 | 2 | 1 | 2 | 2 | 1 | 2 | 2 | 0 | 1 | 0 | 2 | 0 | 1 | 2 |
| C7 | 0 | 1 | 2 | 2 | 0 | 1 | 2 | 2 | 2 | 1 | 2 | 0 | 1 | 1 | 1 | 0 |
| C8 | 0 | 1 | 2 | 0 | 2 | 1 | 1 | 2 | 2 | 1 | 0 | 2 | 0 | 0 | 0 | 2 |
| C9 | 0 | 1 | 2 | 2 | 0 | 2 | 2 | 1 | 0 | 1 | 1 | 2 | 0 | 2 | 0 | 2 |
| C10 | 0 | 1 | 2 | 0 | 2 | 2 | 1 | 0 | 1 | 0 | 2 | 2 | 0 | 2 | 2 | 1 |
| C11 | 0 | 1 | 2 | 2 | 1 | 1 | 2 | 0 | 2 | 0 | 2 | 2 | 1 | 2 | 0 | 0 |
| C12 | 0 | 1 | 2 | 1 | 0 | 0 | 2 | 0 | 1 | 0 | 0 | 0 | 1 | 0 | 1 | 2 |
| C13 | 0 | 1 | 2 | 0 | 1 | 0 | 2 | 1 | 1 | 2 | 2 | 0 | 1 | 0 | 1 | 2 |
| C14 | 0 | 1 | 2 | 1 | 1 | 2 | 2 | 2 | 2 | 0 | 0 | 0 | 2 | 1 | 2 |
| C15 | 0 | 1 | 2 | 0 | 2 | 0 | 1 | 1 | 1 | 2 | 0 | 2 | 2 | 1 | 1 | 0 |
| C16 | 0 | 1 | 2 | 0 | 0 | 2 | 0 | 0 | 0 | 1 | 2 | 2 | 1 | 0 | 2 | 2 |
| C17 | 0 | 1 | 2 | 2 | 2 | 0 | 0 | 2 | 1 | 2 | 0 | 2 | 1 | 1 | 0 | 2 |
| C18 | 0 | 1 | 2 | 0 | 1 | 2 | 1 | 1 | 1 | 2 | 0 | 0 | 0 | 2 | 1 | 2 |
| C19 | 0 | 1 | 2 | 0 | 0 | 1 | 2 | 2 | 2 | 2 | 2 | 0 | 0 | 0 | 0 | 0 |
| C20 | 0 | 1 | 2 | 1 | 0 | 1 | 2 | 2 | 2 | 0 | 1 | 1 | 0 | 2 | 2 | 0 |
| C21 | 0 | 1 | 2 | 2 | 1 | 2 | 1 | 2 | 2 | 2 | 0 | 0 | 2 | 0 | 0 | 1 |
| C22 | 0 | 1 | 2 | 2 | 1 | 0 | 2 | 0 | 0 | 2 | 0 | 2 | 1 | 0 | 2 | 1 |
| C23 | 0 | 1 | 2 | 2 | 1 | 1 | 0 | 2 | 0 | 0 | 2 | 0 | 2 | 2 | 0 |
| C24 | 0 | 1 | 2 | 2 | 1 | 0 | 0 | 2 | 1 | 0 | 0 | 2 | 2 | 0 | 2 |
| C25 | 0 | 1 | 2 | 0 | 2 | 0 | 2 | 1 | 2 | 2 | 2 | 0 | 2 | 0 | 2 | 2 |
| C26 | 0 | 1 | 2 | 2 | 1 | 0 | 1 | 2 | 0 | 2 | 0 | 2 | 1 | 0 | 1 | 0 |
| C27 | 0 | 1 | 2 | 2 | 1 | 2 | 2 | 0 | 0 | 0 | 2 | 0 | 2 | 0 | 0 | 0 |
| C28 | 0 | 1 | 2 | 1 | 0 | 2 | 1 | 0 | 1 | 2 | 1 | 1 | 0 | 0 | 0 | 1 |
| C29 | 0 | 1 | 2 | 1 | 2 | 2 | 2 | 2 | 0 | 1 | 0 | 2 | 2 | 1 | 0 | 2 |
| C30 | 0 | 1 | 2 | 2 | 2 | 0 | 0 | 2 | 2 | 0 | 2 | 2 | 2 | 0 | 0 | 1 |
| C31 | 0 | 1 | 2 | 2 | 0 | 2 | 1 | 2 | 2 | 0 | 2 | 2 | 0 | 2 | 2 | 0 |
| C32 | 0 | 1 | 2 | 2 | 2 | 0 | 2 | 0 | 1 | 0 | 0 | 0 | 0 | 2 | 0 | 0 |
| C33 | 0 | 1 | 2 | 1 | 0 | 2 | 1 | 1 | 1 | 2 | 0 | 2 | 0 | 1 | 1 | 1 |
| C34 | 0 | 1 | 2 | 0 | 2 | 0 | 0 | 0 | 1 | 1 | 2 | 0 | 0 | 0 | 1 | 1 |
| C35 | 0 | 1 | 2 | 2 | 0 | 1 | 1 | 1 | 0 | 0 | 2 | 2 | 0 | 2 | 1 | 1 |
| C36 | 0 | 1 | 2 | 1 | 1 | 0 | 2 | 1 | 1 | 1 | 1 | 1 | 0 | 2 | 0 |
| C37 | 0 | 1 | 2 | 2 | 2 | 2 | 2 | 0 | 2 | 0 | 1 | 1 | 0 | 1 | 1 | 2 |
| C38 | 0 | 1 | 2 | 2 | 0 | 1 | 2 | 2 | 1 | 2 | 0 | 1 | 0 | 2 | 1 | 2 |
| C39 | 0 | 1 | 2 | 1 | 2 | 0 | 1 | 0 | 0 | 0 | 1 | 2 | 1 | 0 | 0 | 2 |
| C40 | 0 | 1 | 2 | 1 | 2 | 0 | 0 | 1 | 0 | 2 | 1 | 2 | 0 | 2 | 1 |
| C41 | 0 | 1 | 2 | 2 | 2 | 2 | 0 | 2 | 2 | 2 | 2 | 2 | 2 | 2 | 0 | 0 |
| C42 | 0 | 1 | 2 | 2 | 0 | 1 | 0 | 2 | 0 | 0 | 0 | 1 | 2 | 0 | 1 | 1 |
| C43 | 0 | 1 | 2 | 0 | 2 | 1 | 0 | 0 | 2 | 1 | 2 | 2 | 2 | 0 | 2 | 0 |

Cell Culture

Experiments were performed using a CHO-S cell line producing a mAb. The cells were first expanded in shake tubes or shake bottles in proprietary medium. Seven days before starting the fed-batch process (day −7), the cells were centrifuged, re-suspended in F1 formulation (lowest level of each component; see Table 1 below) at a concentration of $5×10^6$ cells/mL and then seeded at $0.75×10^6$ cells/mL into 5 square-shaped 96-DWP previously filled with the 376 different blends and 20 controls (final volume per well of 450 μL). All small volume liquid handlings (below 500 μL) were Samples were taken for growth and viability assessment (Guava Easy-Cyte, Merck Millipore). Three passages before the fed-batch inoculation were performed in media with MSX while the fed-batch was performed without. After the expansion phase, the fed-batch process was started with cells seeded at $0.75×10^6$ cells/mL into various media blends, and feeds were added on days 2, 4, 7 and 10. The feeding system consisted of a glucose solution at 400 g/L, a chemically-defined main feed containing over 30 components and a highly concentrated alkaline amino acid solution. Prior to each feeding and at the end of the culture (day 14), samples (below 40 μL) were taken for growth and viability assessment and titer determination.

PDL, IVC, titer and specific productivity (PCD) determination.

PDL was calculated during expansion phase (day −7 to day 0) and during the first two days of fed-batch culture, according to the following formula:

$$PDL = [1/\log 10(2)] \times \log 10(TCD_t/VCD_{t-1}) + PDL_{t-1},$$

with $TCD_t$=total cell density at $time_t$ and $VCD_{t-1}$=viable cell density at $time_{t-1}$.

IVC ($10^6$ cells·day/mL) was calculated during the fed-batch culture, according to the following formula:

$$IVC_t = IVC_{t-1} + (VCD_t + VCD_{t-1})/2 \times \Delta t,$$

where $IVC_t$=IVC at $time_t$, $IVC_{t-1}$=IVC at the previous cell counting (IVC 0=initial IVC=cell density of fed-batch inoculation), $VCD_t$=viable cell density at $time_t$, $VCD_{t-1}$=viable cell density at time t−1 and Δt=difference between time t and t−1.

Titer quantification of the mAb produced during the fed-batch process was performed with the Octet QKe (ForteBio) using Protein A sensors. Each sample was diluted 20× into a dilution buffer (PBS pH=7.4, BSA 0.1 g/L, Tween 20 at 1%). Regeneration buffer was glycine 2M and neutralization buffer was the dilution buffer.

Specific productivity (PCD in pg/cells·day) was calculated according to the following formula:

$$PCD_t = Titer_t / IVC_t.$$

Data Analysis

Spreadsheet Analysis

Data were compiled in a spreadsheet and different media blending conditions were scored and ranked according to their potential to improve process performance. First, an improvement score was determined for each output (IVC, viability, titer, PDL), defined as the percentage of improvement vs. control. A global score was then calculated for each condition by adding individual scores previously normalized against maximum titer score (normalization was performed against maximum titer because titer showed a higher percentage of improvement than other outputs). Ranking global scores of all blending conditions enabled determination of the best formulations. For those conditions having a global score of zero, ranking was based on the amount of titer.

Analysis by Design Expert

Design Expert software (V8.1, StatEase) was used to analyze each output (PDL, IVC, and titer mainly), generating reduced quadratic mixture models for each one and at each time point. The analysis of variance (ANOVA) of each model indicated the main factors (key formulations) with a significant influence on PDL, IVC and titer. A square root transformation was applied to titer and IVC and a power transformation to PDL to improve their models. Models were then used to predict best mixtures from the 16 formulations to maximize both growth and production.

An "average best" mixture was designed.

Analysis by SIMCA-P++

The analysis was based on MVA and used SIMCA-P++ software (V12, U-Metrics). PLS regressions were performed for each output to study the effects of each component in order to identify key components. To detect a possible correlation between components of the MVA, a correlation matrix was drawn and correlation factors were determined. A correlation was considered as strong if the correlation factor was above 0.8, medium if it was between 0.6 and 0.8, and negligible if it was below 0.6.

Results

Generalities

Blends were tested on both the cell expansion and the fed-batch production phases, ensuring that the best production media identified can also be used as expansion media. The resulting data was analyzed by three approaches, a scoring and ranking of media blends based on their potential to improve cell growth and productivity, and two statistical approaches using Design Expert and multivariate analysis (MVA). FIG. 1 depicts a high-throughput media blending method for the medium development of a fed-batch cell culture process. Sixteen media formulations were designed from 43 of 47 components. Media blending following a custom-made mixture DoE resulted in 376 different blends which were evaluated in 96-deepwell plates (DWP) for cell culture performance in fed-batch. Data were first analyzed empirically, and then by statistical methodologies.

Figure 2:
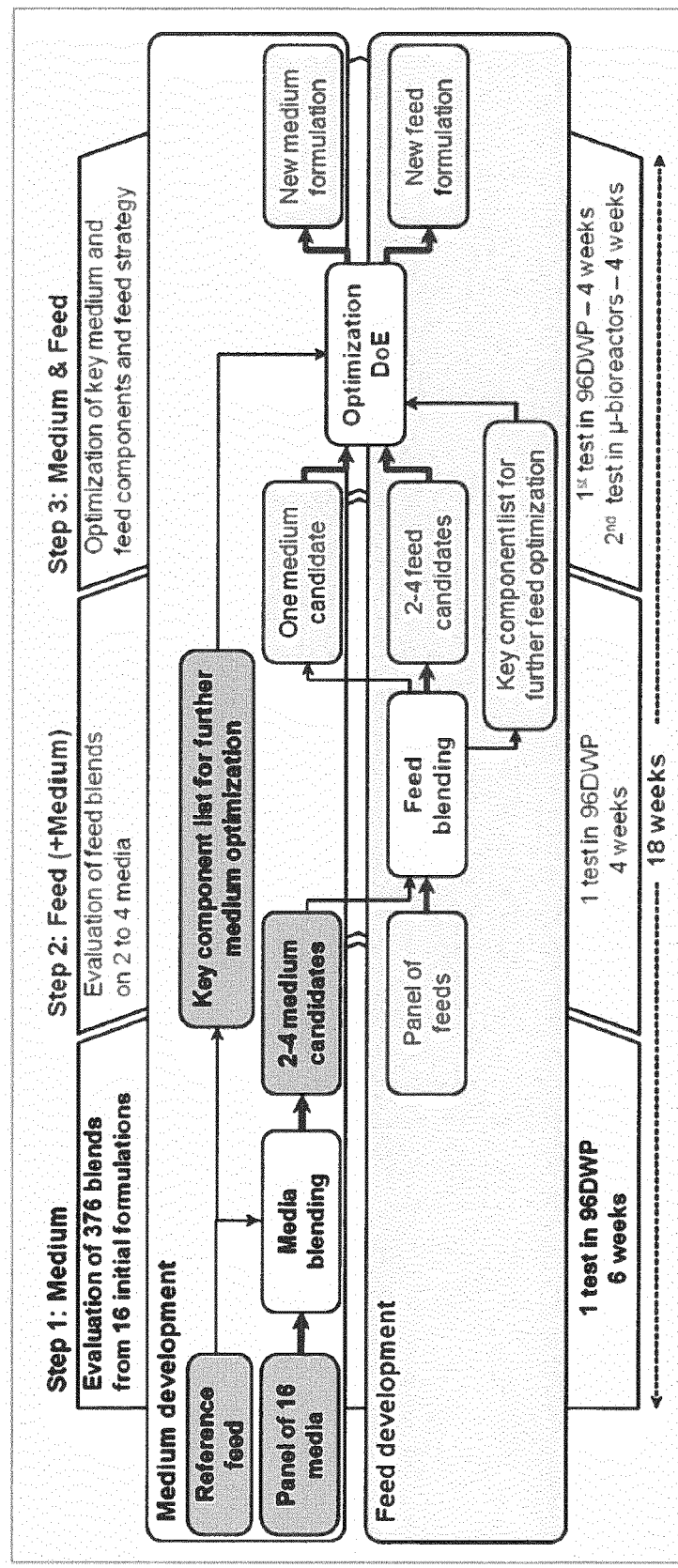
FIG. 2 shows an improved development strategy using high-throughput cell culture methods based on media and feed blending in accordance with an embodiment of the present invention.

The robustness of the blending method was verified by repeating the entire blending experiment under similar conditions. This study represents the first of a global three-step strategy that enables development and optimization of a fed-batch process in 18 weeks, as shown in FIG. 2.

In the first step basal medium is optimized while keeping the feed constant. In the next step, media candidates identified during the first step are tested in a second round of experiments in combination with a panel of feed blends generated from a certain number of feed formulations. The third step consists of optimizing key media.

Media Formulation Design and Preparation.

A first-generation proprietary medium formulation designed for an industrial fed-batch process was further improved by media blending. The goal of this experiment was to optimize the concentrations of 43 of 47 components. Of the four remaining components, glucose and $NaHCO_3$ were kept constant, while NaCl and NaOH were used for osmolality and pH adjustments, respectively. Sixteen media formulations were designed with the 43 components (see Table 1 below). For each component, three levels were chosen (low=0, intermediate=1 and high=2). The components and their testing ranges are given in Table 1. To choose the component concentration for each level, a preliminary cell culture experiment with concentrated proprietary medium (0.25 to 3×) was performed, and cell growth and titer were measured. Based on these experimental data, as well as on component concentrations in proprietary media formulations at 1× and scientific knowledge from literature, concentrations corresponding to the three levels were selected. Level 1 was close to the concentrations found in the first-generation proprietary medium (Ctrl 1) for most of the components, and F2 with all components at level 1 was considered as a second control (Ctrl 2). These controls were performed to assess experiment and plate-to-plate variability. Except for the first three formulations with all components at the same level (respectively 0, 1 and 2), each formulation was randomly designed regarding each component level.

Eighty random designs of the 16 formulations were generated and assessed for correlations between components. The design that best minimized these correlations was selected in order to maximize the design space of the experiment.

Process Performance in Deepwell Plates.

The design and mixing of the 16 formulations resulted in 376 different media blends that were added into 96-deepwell plates (DWP) containing CHO cells producing a mAb, using a robotic platform. Examples of media blending mixtures in some of the 396 wells (376 media blends and 20 controls) are provided in Table 3.

TABLE 3

Examples of blending mixtures - 12 blending mixture recipes from 16 formulations are shown as examples. one control (Ctrl 1: proprietary medium) is shown in run 3 and another control (Ctrl 2: F2 formulation: mid-point of each component) in Run 95

| Run | Well | Plate | Ctrl 1 | F1 | F2 | F3 | F4 | F5 | F6 | F7 | F8 | F9 | F10 | F11 | F12 | F13 | F14 | F15 | F16 |
|---|---|---|---|---|---|---|---|---|---|---|---|---|---|---|---|---|---|---|---|
| 2 | A02 | 1 | 0 | 0 | 0 | 0 | 0 | 0 | 0 | 0 | 0.3 | 0 | 0.7 | 0 | 0 | 0 | 0 | 0 | 0 |
| 3 | A03 | 1 | 1 | 0 | 0 | 0 | 0 | 0 | 0 | 0 | 0 | 0 | 0 | 0 | 0 | 0 | 0 | 0 | 0 |
| 16 | B06 | 1 | 0 | 0 | 0 | 0 | 0 | 0 | 0 | 0 | 0 | 0 | 0.3 | 0.7 | 0 | 0 | 0 | 0 | 0 |
| 94 | B04 | 2 | 0 | 0 | 0 | 0 | 0 | 0.3 | 0 | 0 | 0.7 | 0 | 0 | 0 | 0 | 0 | 0 | 0 | 0 |
| 95 | B05 | 2 | 0 | 0 | 1 | 0 | 0 | 0 | 0 | 0 | 0 | 0 | 0 | 0 | 0 | 0 | 0 | 0 | 0 |
| 130 | E10 | 2 | 0 | 0 | 0 | 0 | 0 | 0 | 0 | 0 | 0 | 0.5 | 0 | 0 | 0 | 0 | 0.5 | 0 | 0 |
| 231 | H01 | 3 | 0 | 0 | 0 | 0 | 0 | 0 | 0 | 0 | 0 | 0.5 | 0 | 0 | 0 | 0.5 | 0 | 0 | 0 |
| 239 | H09 | 3 | 0 | 0 | 0.7 | 0 | 0 | 0 | 0 | 0 | 0 | 0 | 0 | 0 | 0 | 0 | 0 | 0 | 0.3 |
| 249 | A09 | 4 | 0 | 0 | 0 | 0 | 0.3 | 0 | 0.7 | 0 | 0 | 0 | 0 | 0 | 0 | 0 | 0 | 0 | 0 |
| 311 | H01 | 4 | 0 | 0 | 0 | 0.5 | 0 | 0 | 0 | 0 | 0 | 0 | 0.5 | 0 | 0 | 0 | 0 | 0 | 0 |
| 398 | H08 | 5 | 0 | 0 | 0 | 0 | 0 | 0 | 0 | 0 | 0 | 0 | 0.7 | 0 | 0.3 | 0 | 0 | 0 | 0 |
| 399 | H09 | 5 | 0 | 0 | 0 | 1 | 0 | 0 | 0 | 0 | 0 | 0 | 0 | 0 | 0 | 0 | 0 | 0 | 0 |

Figure 3:
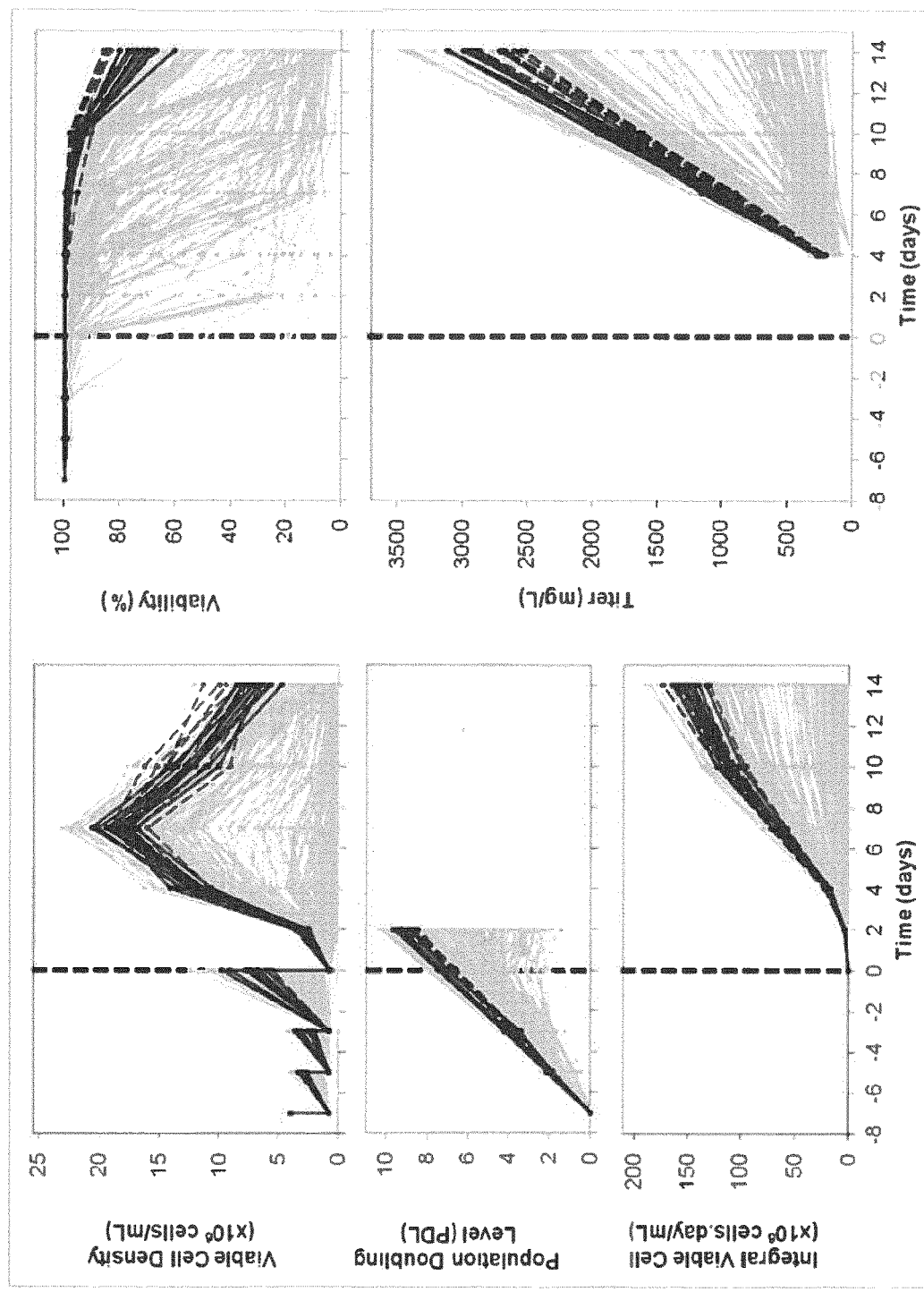
FIG. 3 shows the viable cell density (VCD), viability (%), integral viable cell density (IVC), population doubling level (PDL) and titer for 376 media blends and 20 controls prepared in accordance with an embodiment of the present invention.

Mixtures were tested on both cell expansion and fed-batch production phases. FIG. 3 shows the process performance obtained with the 376 different media blends (gray lines) and 20 controls (dashed black lines: Ctrl 1, full black lines: Ctrl 2) in terms of population doubling level (PDL), cell growth, viability, integral of viable cells (IVC), and titer. Data from day −7 to day 14 for viable cell density and viability, from day −7 to day 2 for pDL and from day 0 to day 14 for IVC and titer. All outputs showed broad ranges of results, depending on tested conditions. During the expansion phase, some media blends were able to increase cell growth rate by 20% as shown by PDL data, and to reduce doubling time from 24 h to 20 h in controls (data not shown). This was confirmed during the production phase, with up to 20% IVC improvements, from 156 (for controls) to 190×10$^6$ cells·day/mL (for the best condition).

Several conditions did not allow growth or induced important cell aggregation. Large variations in growth profiles were observed, from no growth to 23.7×10$^6$ cells/mL (controls at 18.0×10$^6$ cells/mL). Of approximately 50 conditions improved cell growth, only 10 showed equal or increased cell viability at harvest. This might be due to new nutrient limitations resulting from improved growth, and to the same feed regimen applied to all conditions. Regarding the titer, an improvement of up to 40% was observed, with a maximum titer around 3.7 g/L. Ctrl 2 (F2 with all components at level 1) showed a significant and robust titer improvement (around 13%) compared with Ctrl 1.

Data analysis Process.

Figure 4:
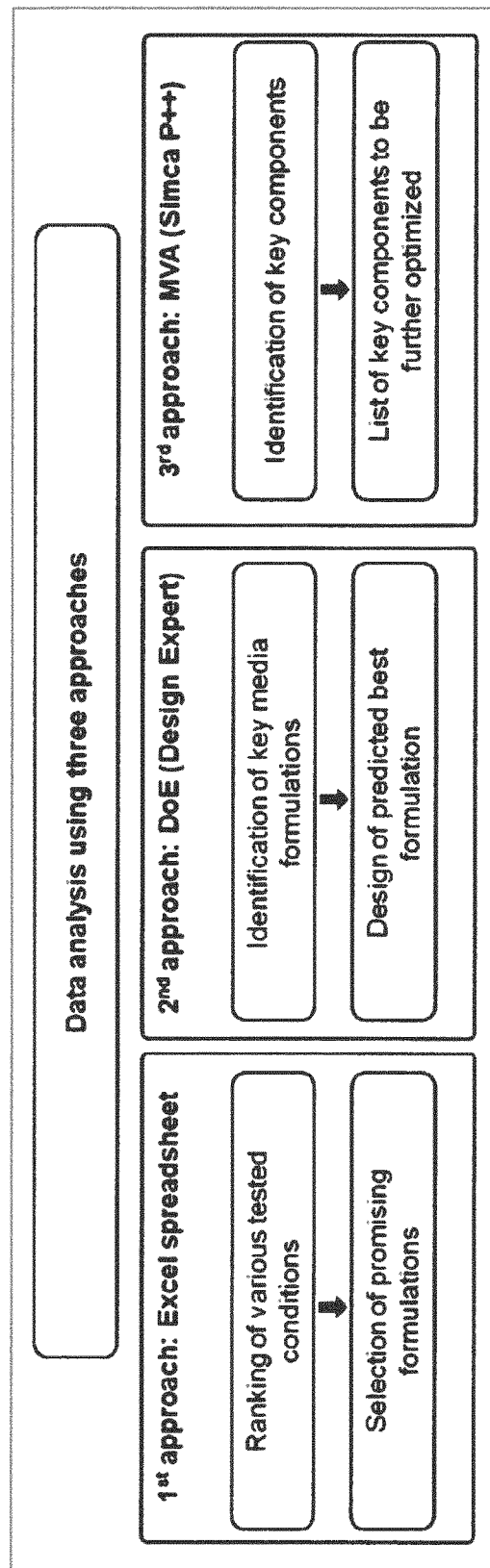
FIG. 4 shows three possible approaches for data analysis in accordance with the present invention.

To get the best output of the large data set obtained from the media blending experiment, three options were chosen, as shown in FIG. 4. The first level of analysis was performed in Excel with the determination of an improvement score for each output vs. control, a global score for each mixture and a rank to select best conditions. The second level of analysis was performed using Design expert, modelling each output to predict best formulations. The third level of analysis was performed by multivariate analysis using SIMCA-p++ to identity key components.

An example of the first approach, analyzing data of individual outputs (viable cell density, titer, IVC, PDL, and viability) for each condition on a spreadsheet, is given in Table 4. This table shows process performance data obtained for some of the blending experiment conditions (described in Table 3), and a calculated improvement score for each output and a global score and rank for each condition. This approach represents a quick way to select the most promising conditions.

TABLE 4

Examples of process performance data and of scores and ranks - the left part of the table shows data for IVC, viability and titer on day 14 and PDL on day 2 for cells incubated with some of the 376 blending mixtures (see Table 3 for blending mixture recipes). the right part of the table shows individual improvement scores for IVC, viability, titer and pDL vs. control (expressed in %), the global score for each blending mixture (corresponding to the addition of individual scores normalized vs. maximum titer score), and the rank based on the global score.

| | | | | IVC | Viability | Titer | Improvement score for each output (%) | | | | | Global | |
|---|---|---|---|---|---|---|---|---|---|---|---|---|---|
| Run | Well | Plate | | (×10$^4$ cells · day/mL) | (%) | (mg/L) | PDL | IVC | Viability | Titer | PDF | Score | Rank |
| 2 | A02 | 1 | | 157 | 64 | 2442 | 8.8 | 1.0 | — | — | — | 1.7 | 127 |
| 3 | A03 | 1 | Ctrl 1 | 162 | 83 | 2601 | 8.7 | 3.9 | 1.3 | — | — | 12.3 | 95 |
| 16 | B06 | 1 | | 180 | 89 | 2470 | 9.7 | 15.5 | 8.7 | — | 8.9 | 81.1 | 6 |
| 94 | B04 | 2 | | 12 | 31 | 583 | 4.6 | — | — | — | — | 0 | 320* |
| 95 | B05 | 2 | Ctrl 2 | 145 | 68 | 3126 | 9.5 | — | — | 16.8 | 6.6 | 47.6 | 27 |
| 130 | E10 | 2 | | 185 | 63 | 3468 | 10 | 18.7 | — | 29.6 | 12.8 | 117 | 1 |
| 231 | H01 | 3 | | 167 | 67 | 3657 | 9.5 | 7.2 | — | 36.6 | 7.7 | 100.4 | 3 |
| 239 | H09 | 3 | | 175 | 84 | 2869 | 10.0 | 12.4 | 2.0 | 7.2 | 12.4 | 69.9 | 11 |
| 249 | A09 | 4 | | 30 | 17 | 778 | 7.0 | — | — | — | — | 0 | 261* |
| 311 | H01 | 4 | | 186 | 60 | 3278 | 10.3 | 19.1 | — | 22.5 | 16.6 | 111.9 | 2 |
| 398 | H08 | 5 | | 149 | 68 | 2619 | 9.2 | — | — | — | 3.7 | 7.8 | 110 |
| 399 | H09 | 5 | | 105 | 60 | 2686 | 8.8 | — | — | 0.3 | — | 0.7 | 131 |

Figure 5:
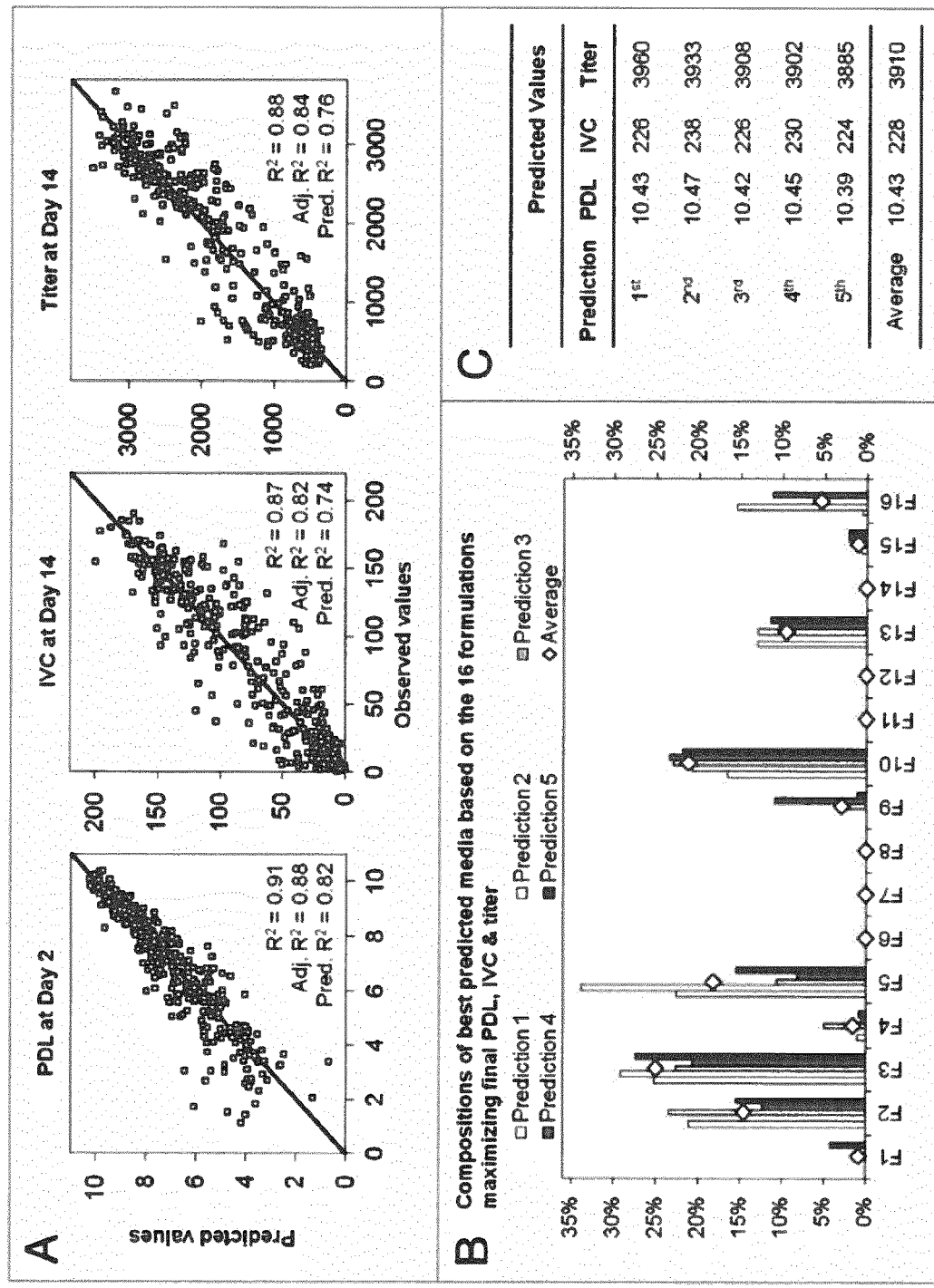
FIG. 5 shows data processing using a statistical design analysis program in accordance with an embodiment of the present invention.

*For those conditions having a global score of zero, ranking was based on the amount of titer The two other approaches used statistical tools enabling a more in-depth data analysis. A prediction of the best mixtures maximizing both cell growth and titer was obtained using the Design Expert software. Each output was modelled regarding the different formulation mixtures. Main effect and the 1st level of interactions were assessed by ANOVA. A good correlation between experimental values and predictions from the model was obtained for PDL at day 2, IVC ($\times 10^6$ cells·day/mL) and titer (mg/L) at day 14 with $R^2$ around 0.9 and predicted-$R^2$ between 0.7 and 0.8 (FIG. 5A), enabling best mixture predictions. FIG. 5B shows the composition of the 5 best predicted media, plus a 6th medium representing the average of the 5 best predicted media, based on 16 formulations and maximizing final PDL, IVC and titer. FIG. 5C shows predicted values for PDL, IVC and titer for the 5 best predictions and for the average of these 5 best predictions.

Figure 6:
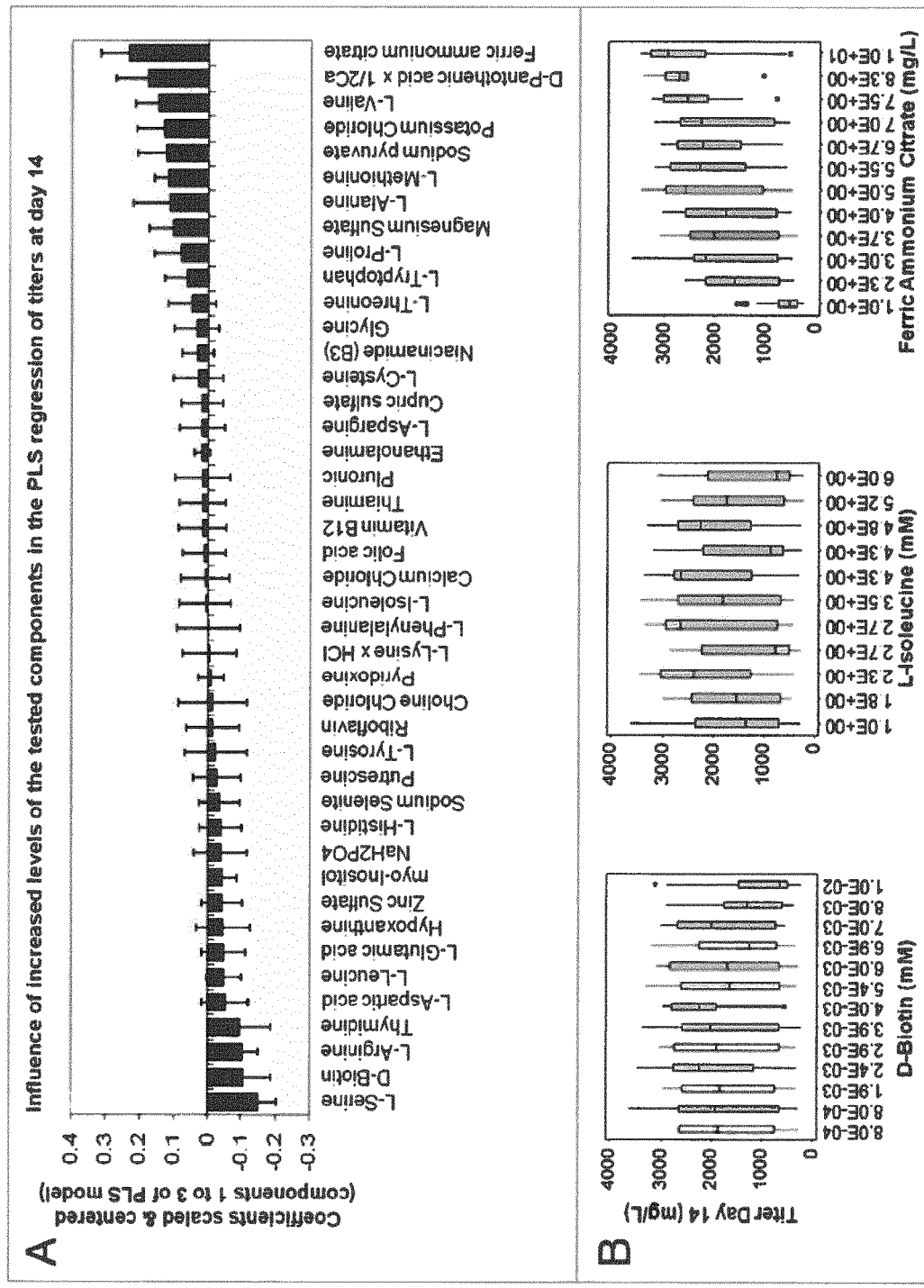
FIG. 6 shows the results of multi-variable analysis (MVA) in accordance with an embodiment of the present invention.

The third level of analysis, based on MVA, used SIMCA-P++ software. A model was created for the titer using partial least squares (PLS) regressions. Three components were used to create a relatively good model with respect to the low number of tested conditions compared with the number of evaluated factors. The $R^2$ (an indication of how well the model fits experimental data) and the $Q^2$ (an estimation of the model predictive ability) for the 3rd component were 0.514 and 0.438, respectively. FIG. 6A shows the influence of individual components on titer on day 14 determined by PLS regressions. Ferric ammonium citrate, pantothenic acid and valine appeared among components having a strong positive effect on titer, while serine, biotin and arginine were among those having a negative effect. Scatter plots of 3 components with either a highly positive (ferric ammonium citrate; on graph, "*" represents outliers), a highly negative (Biotin) or a neutral (Isoleucine) effect on titer are shown in FIG. 6B. Ferric ammonium citrate showed poor performance at low concentration (titer less than 1 g/L at 1 mg/L), but then titer increased to stabilize around 3 g/L at 5 mg/L. Best results were obtained between 7.5 and 10 mg/L. The titer was not substantially affected by the biotin concentration between 0.8 and 4 µM, but decreased at higher concentrations. On the other hand, isoleucine had no clear effect on titer between 1 and 6 mM. Potentially, there might be additional components with a significant positive or negative effect.

The PLS analysis alone will not be able to reliably attribute the effects to all the components, because of existing correlations between certain samples. To assess this, a correlation matrix was drawn (data not shown). A high correlation was observed for two pairs of factors, methionine vs. asparagine and putrescine vs. glutamic acid. Candidate components for further optimization were selected based on two criteria, their tendency to influence the model and their correlation with other important factors in the test. In total, 13 factors can be proposed based on these criteria. Factors influencing the model are ferric ammonium citrate, pantothenic acid, valine, methionine, arginine, biotin and serine, while factors correlating with an important factor in the MVA are aspartic acid, asparagine, cupric sulfate, cysteine, Vitamin B12 and sodium selenite (correlates with a factor that correlates with an important factor in the MVA). Further optimization of these factors using, for example, a DoE approach should lead to the identification of media formulations with potentially improved performance.

Robustness of the media blending method.

Figure 7:
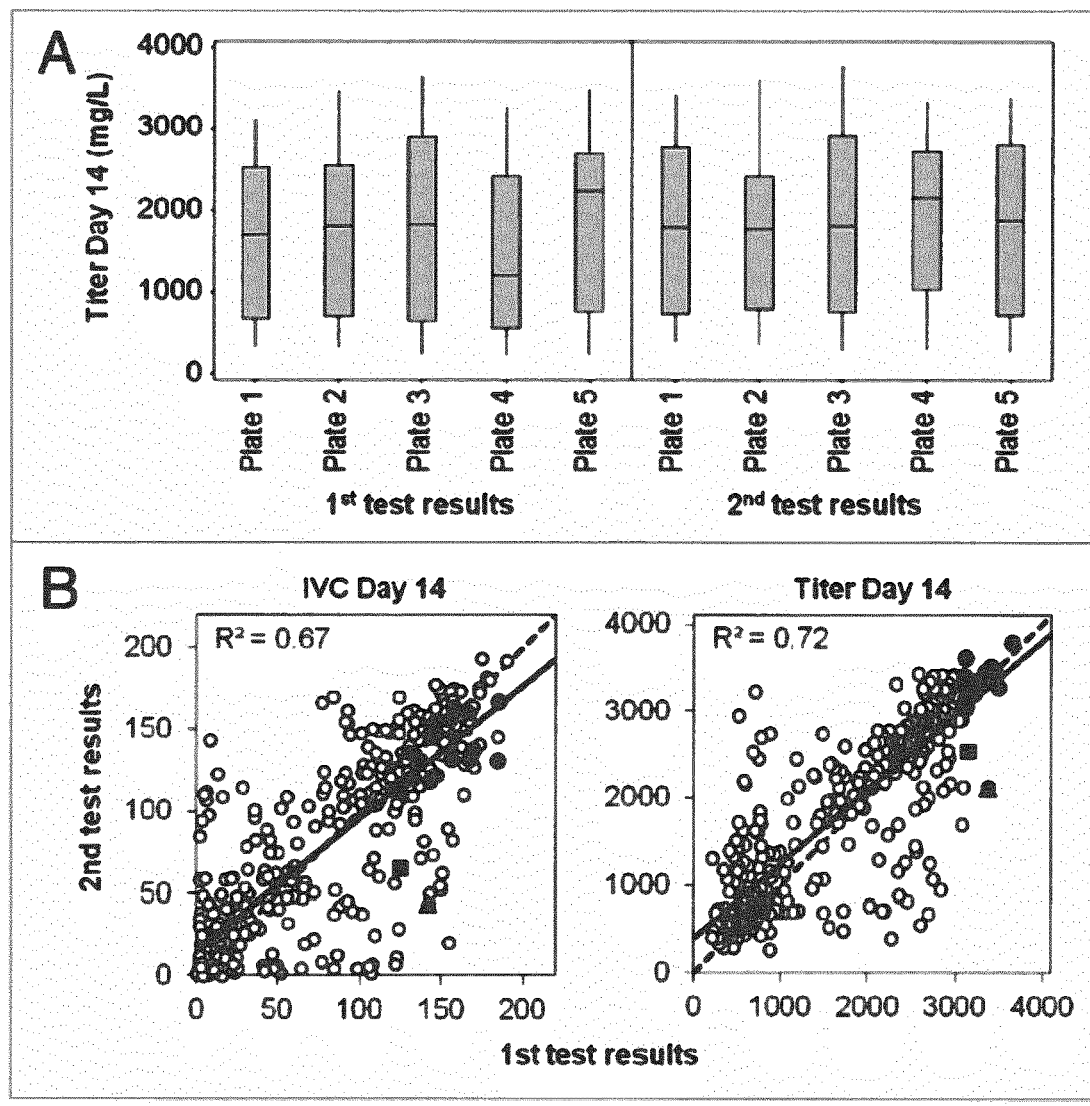
FIG. 7 shows data analysis for determining robustness of the blending method in accordance with an embodiment of the present invention.

To evaluate the robustness of the method, the experiment with media blends was repeated under similar conditions. FIG. 7A shows the final titer distribution on day 14 for each of the 5 plates of the 1st and the 2nd blending experiment. Globally, titer distribution was comparable for all plates of both experiments; only plate 4 of the 1st experiment showed lower titers, which might be linked to a technical problem such as wrong dilution or wrong pipetting. Nevertheless, as shown in FIG. 7B, when considering the 20 best conditions obtained for titer and IVC from the 1st experiment, 18 were in close correlation with data obtained in the $2^{nd}$ experiment, and the $R^2$ was around 0.7 for both IVC and titer (open circles represent 376 tested conditions and black symbols 20 best conditions for titer in the first experiment; circles represent the 18 conditions that were highly reproducible whereas the square and the triangle represent the two conditions lacking reproducibility). This demonstrates the robustness of the blending method for the best performing conditions. More variations were observed for conditions inducing lower performance, linked to cell clumping, metabolic factors or physical parameters. The next step after identification of the best performing media formulations will be to test them at larger scale to confirm predictability.

All references cited herein, including journal articles or abstracts, patent applications or any other references, are hereby incorporated by reference in their entireties, including all data, tables, figures and text presented in the cited references. Additionally, the entire contents of the references cited within the references cited herein are also entirely incorporated by reference.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation.

The invention claimed is:

1. A cell culture medium comprising: 1.7 to 10 mM of $NaH_2PO_4$, 2 to 9 mM of L-Leucine, 1 to 6 mM of L-Lysine, 0 to 3 mM of Glycine, 0.4 to 2 mM of L-Methionine, 1 to 4 mM of L-Glutamic acid, 0.5 to 3 mM of L-phenylalanine, 0.7 to 6 mM of L-proline, 0.7 to 6 mM of L-threonine, 0.5 to 2 mM of L-tryptophan, 1 to 7 mM L-Valine, 0.1 to 1.5 mM of Magnesium Sulfate, 0.1 to 1.05 mM of Calcium Chloride, 0.07 to 0.7 mM of myo-Inositol, 0.8 to 4 mM of Sodium pyruvate, 0.0008 to 0.004 mM of D-Biotin, 0.1 to 1 mM of Choline Chloride, 3 to 9 mM of L-Asparagine, 0.006 to 0.04 mM of Folic acid, 0.03 to 0.15 mM of Niacinamide (B3), 0.015 to 0.15 mM of D-pantothenic acid×½Ca, 1 to 8 mM of L-Serine, 1 to 10 mM of Potassium Chloride, 0.005 to 0.05 mM of Pyridoxine, 0.8 to 2.4 mM of L-Aspartic acid, 0.0003 to 0.003 mM of Riboflavin, 0.008 to 0.04 mM of Thiamine, 7.5 to 10 mg/L of Ferric ammonium citrate, 0.0003 to 0.004 mM of Vitamin B12, 0.008 to 0.04 mM of Hypoxanthine, 0.0015 to 0.006 mM of Thymidine, 0.006 to 0.03 mM of Putrescine, 0.1 to 0.5 mM of Ethanolamine, 0.004 to 0.02 mM of Zinc Sulfate, 0.00004 to 0.0008 mM of Cupric sulfate, 0.5 to 2.0 g/L of poloxamer, 0.7 to 3 mM of L-tyrosine, 0.00001 to 0.00006 mM of Sodium Selenite, 0 to 3 mM of L-Alanine, 1 to 3 mM of L-Arginine, 1 to 3 mM of L-Cysteine, 0.4 to 3 mM of L-Histidine, and 1 to 6 mM of L-Isoleucine.

2. The medium according to claim 1, further comprising glucose, $NaHCO_3$, NaCl, NaOH, or combinations thereof.

3. The medium according to claim 2, wherein the glucose is at a concentration of about 6 g/L and $NaHCO_3$ is at a concentration of about 2 g/L.

4. The medium according to claim 1, wherein the osmolality of the medium ranges from 300 to 330 mOsm/kg.

5. The medium according to claim 1, wherein the pH of the medium ranges from 6.0-8.0.

6. The medium according to claim 1, said medium containing Glycine or L-Alanine or both.

7. A method for culturing mammalian cells to obtain a product comprising growing the cells in the medium of claim 1.

8. A method of producing a protein comprising growing a recombinant CHO cell line in the medium of claim 1 and recovering the protein expressed by said cell line from said medium.

9. The medium according to claim 1, wherein said medium is serum-free and protein-free.

* * * * *

UNITED STATES PATENT AND TRADEMARK OFFICE
CERTIFICATE OF CORRECTION

PATENT NO. : 10,138,467 B2  
APPLICATION NO. : 15/028989  
DATED : November 27, 2018  
INVENTOR(S) : Herve Broly et al.

Page 1 of 1

It is certified that error appears in the above-identified patent and that said Letters Patent is hereby corrected as shown below:

In the Specification

Column 6,  
Line 38, "NaHCo3" should read --$NaHCO_3$--.

Column 7,  
Line 6, "NaHCo3" should read --$NaHCO_3$--.

Column 12,  
Line 16, "component. except for" should read --component. Except for--.

Column 15,  
Line 3, "examples. one control" should read --examples. One control--.

Column 16,  
Line 43, "ranks – the left" should read --ranks – The left--.

Column 16,  
Line 50, Table 4 Column 12 Heading, "PDF" should read --PDL--.

Signed and Sealed this  
Thirtieth Day of July, 2019

Andrei Iancu  
*Director of the United States Patent and Trademark Office*